(12) United States Patent
Hu et al.

(10) Patent No.: US 11,703,498 B2
(45) Date of Patent: Jul. 18, 2023

(54) THREE-PARAMETER STRENGTH REDUCTION METHOD FOR SLOPE STABILITY EVALUATION

(71) Applicant: Shaoxing University, Shaoxing (CN)

(72) Inventors: Yunjin Hu, Shaoxing (CN); Zhen Zhong, Shaoxing (CN); Huicai Gao, Shaoxing (CN); Zhenbo Wu, Shaoxing (CN); Huan Yang, Shaoxing (CN)

(73) Assignee: Shaoxing University, Shaoxing (CN)

( * ) Notice: Subject to any disclaimer, the term of this patent is extended or adjusted under 35 U.S.C. 154(b) by 309 days.

(21) Appl. No.: 17/174,550

(22) Filed: Feb. 12, 2021

(65) Prior Publication Data

US 2021/0263004 A1 Aug. 26, 2021

(30) Foreign Application Priority Data

Feb. 17, 2020 (CN) .......................... 202010095817.7

(51) Int. Cl.
*G01N 3/08* (2006.01)
*G01N 3/24* (2006.01)
(Continued)

(52) U.S. Cl.
CPC ............. *G01N 33/24* (2013.01); *E02D 17/20* (2013.01); *G01N 3/08* (2013.01); *G01N 3/24* (2013.01);
(Continued)

(58) Field of Classification Search
CPC ............ G01N 33/24; G01N 3/08; G01N 3/00; G01N 3/24; G01N 2203/0026;
(Continued)

(56) References Cited

U.S. PATENT DOCUMENTS

| | | | | |
|---|---|---|---|---|
| 2003/0082014 A1* | 5/2003 | Kang | ..................... | E02D 17/207 405/287.1 |
| 2015/0168597 A1* | 6/2015 | Bai | ........................ | G01V 99/00 703/10 |
| 2017/0268874 A1* | 9/2017 | Kasahara | ................. | G01C 9/02 |

OTHER PUBLICATIONS

Zhao et al. "Seismic displacement along a log-spiral failure surface with crack using rock Hoek-Brown failure criterion", May 15, 2017, Elsevier, pp. 74-85. (Year: 2017).*
(Continued)

*Primary Examiner* — Mohamed Charioui
(74) *Attorney, Agent, or Firm* — MagStone Law, LLP; Enshan Hong

(57) ABSTRACT

Disclosed is a three-parameter strength reduction method for slope stability evaluation. The present disclosure reflects the difference in the attenuation and contribution of the cohesion, internal friction angle and tensile strength in the process of slope instability by reducing the three parameters by different reduction factors. Based on the sudden change of the characteristic point displacement of the slope as a criterion of slope instability, the present disclosure derives the fitting relationship between the characteristic point displacement and the cohesion reduction factor. The present disclosure assumes that the comprehensive safety factor satisfies a linear relationship with the cohesion reduction factor, the internal friction angle reduction factor and the tensile strength reduction factor and derives the relationship between the comprehensive safety factor and the cohesion reduction factor. Finally, the present disclosure summarizes and proposes a three-parameter strength reduction method and provides the steps for analyzing the slope stability through this method.

4 Claims, 2 Drawing Sheets

(51) Int. Cl.
    *G06F 17/11*     (2006.01)
    *G01N 33/24*     (2006.01)
    *E02D 17/20*     (2006.01)

(52) U.S. Cl.
    CPC ...... *G06F 17/11* (2013.01); *G01N 2203/0026* (2013.01)

(58) Field of Classification Search
    CPC ........ G01N 2203/0014; G01N 2203/00; E02D 17/20; E02D 17/00; G06F 17/12; G06F 17/11; G06F 17/10; G06Q 10/0639
    See application file for complete search history.

(56)            References Cited

OTHER PUBLICATIONS

Zhong et al. "Slope Stability Analysis Using Limit Equilibrium Method in Nonlinear Criterion", 2015, Hindawi Publishing Corporation, vol. 2015, Article ID 419636, pp. 1-7. (Year: 2015).*

Gong et al. "Stability Analysis of Soil Embankment Slope Reinforced with Polypropylene Fiber under Freeze-Thaw Cycles", Jan. 21, 2019, Hindawi, vol. 2019, Article ID 5725708, pp. 1-10. (Year: 2019).*

\* cited by examiner

THREE-PARAMETER STRENGTH REDUCTION METHOD FOR SLOPE STABILITY EVALUATION

RELATED APPLICATIONS

This application claims priority to China Patent Application No. 202010095817.7, filed with the China National Intellectual Property Administration (CNIPA) on Feb. 17, 2020, which is incorporated herein by reference in its entirety.

TECHNICAL FIELD

The present disclosure belongs to the field of slope stability evaluation, and particularly relates to a three-parameter strength reduction method for slope stability evaluation and provides a reliable method for calculating a slope stability safety factor.

BACKGROUND

Slope safety is related to the safety of people's lives and property. As an important method to solve the safety factor, the strength reduction method is widely used in slope stability evaluation. However, the traditional strength reduction method has some problems in analyzing slope stability. 1) The cohesion c and internal friction angle $\varphi$ are usually reduced by the same reduction factor, without considering the difference in the contribution and attenuation of the two shear strength parameters in slope instability. 2) The reduction of the tensile strength $\sigma_t$ of the rock-soil mass is not considered, and the actual tensile failure of the slope is not accurately reflected. In order to solve the first problem, some scholars have proposed a Double Reduction Method (DRM) which adopts a mechanism of matching reduction and a comprehensive safety factor determination method. The DRM is to reduce the cohesion and the internal friction angle by different reduction factors. The mechanism of matching reduction defines the relationship to be satisfied between the reduction factors $F_c$ and $F_\varphi$ of the cohesion and the internal friction angle. However, the rationality of the linear mechanism of matching reduction needs further verification, and the nonlinear mechanism of matching reduction lacks universality. The comprehensive safety factor determination method clarifies how to comprehensively evaluate the slope stability based on $F_c$ and $F_\varphi$, but the determination methods of different comprehensive safety factors vary greatly and lack sufficient theoretical basis and clear physical meaning. In order to solve the second problem, some scholars have proposed to take into account the tensile failure by reducing the tensile strength. At present, there are mainly two tensile strength reduction methods. 1) The cohesion, internal friction angle and tensile strength are reduced by the same reduction factor, but this does not consider the difference in the contribution and attenuation of different parameters. 2) The tensile strength is reduced based on the asynchronous reduction of c and $\varphi$, but the comprehensive safety factor determination method of the DRM is still used, ignoring the influence of the tensile strength reduction on the safety factor.

In the process of slope instability, the slope suffers both shear failure and tensile failure. When the existing strength reduction method uses the comprehensive safety factor to evaluate slope stability, it does not consider the influence of the tensile strength reduction on the safety factor. It does not derive the calculation formula of the comprehensive safety factor from the perspective of instability criterion, and thus results in insufficient theoretical basis, unclear physical meaning and inaccurate comprehensive safety factor. Therefore, it is necessary to propose a reduction method that takes into account the tensile failure and reflects the different attenuation of cohesion and internal friction angle, and propose a proper calculation formula of the comprehensive safety factor to accurately and objectively evaluate slope stability. The present disclosure is thus proposed.

SUMMARY OF THE INVENTION

In order to solve the problems existing in the prior art, an objective of the present disclosure is to provide an improved strength reduction method for slope stability evaluation. This method reduces c, $\varphi$, $\sigma_t$ by different reduction factors to reflect the different contributions and attenuation of different parameters. This method takes the sudden change of the characteristic point displacement of the slope as a criterion of slope instability, and determines the comprehensive safety factor according to the different reduction factors of c, $\varphi$, $\sigma_t$, so as to accurately and objectively evaluate the slope stability.

To achieve the above objective, the present disclosure adopts the following technical solution:

A three-parameter strength reduction method for slope stability evaluation, including the following steps:

step 1, reducing a shear strength parameter cohesion c by a reduction factor $F_c$, reducing an internal friction angle $\varphi$ by a reduction factor $F_\varphi$, and deriving a mechanism of matching reduction $$K = \frac{F_\varphi}{F_c}$$

to obtain a relational expression of $F_\varphi$ and $F_c$;

step 2, substituting the reduced shear strength parameters cohesion and internal friction angle into a uniaxial tensile strength expression to obtain a reduced tensile strength, and dividing a tensile strength before reduction by the tensile strength after reduction to obtain a reduction factor $F_t$ of the tensile strength;

step 3, assuming that a comprehensive safety factor $F_s$ satisfies a linear relationship with $F_c$, $F_\varphi$ and $F_t$, then obtaining an expression of $F_s$ based on a sudden change of a displacement of a characteristic point of a slope as a criterion of slope instability, and fitting a displacement curve of the characteristic point of the slope to obtain a relational expression between $F_s$ and $F_c$ and a relational expression between the displacement $\zeta$ of the characteristic point and $F_c$; and step 4, determining that the slope is unstable based on the slope instability criterion when the characteristic point displacement of the slope changes suddenly, and substituting the obtained $F_c$ into the relational expression between $F_s$ and $F_c$ to obtain the comprehensive safety factor $F_s$.

Further, the uniaxial tensile strength expression is:

$$\sigma_t = \frac{2c}{\tan\varphi + \sqrt{1 + \tan^2\varphi}} \quad (1)$$

where, $\sigma_t$ is an initial tensile strength of a rock-soil mass, and the reduced tensile strength is shown in Eq. (2):

$$\sigma_{ti} = \frac{2c_i}{\tan\varphi_i + \sqrt{1+\tan^2\varphi_i}} = \frac{\lambda\sigma_t}{1+\sqrt{\gamma F_{ci}^2+1}} \quad (2)$$

where, $\sigma_{ti}$ is a corresponding tensile strength in an i-th reduction step; $c_i$, $\varphi_i$ are corresponding cohesion and internal friction angle in the i-th reduction step, respectively; $F_{ci}$ is a cohesion reduction factor in the i-th reduction step; $\lambda = K + K\sqrt{1+\cot^2\varphi}$, $\gamma = K^2 \cdot \cot^2\varphi$, which are respectively a constant greater than 0.

The tensile strength reduction factor $F_t$ is:

$$F_t = \frac{1+\sqrt{\gamma \cdot F_c^2+1}}{\lambda} \quad (3)$$

Further, the linear relationship between the comprehensive safety factor $F_s$ and $F_c$, $F_\varphi$ and $F_t$ is:

$$F_s = m_1 \cdot F_c + m_2 \cdot F_\varphi + m_3 \cdot F_t \quad (4)$$

where, $m_1$, $m_2$, $m_3$ are undetermined coefficients, and substituting $$K = \frac{F_\varphi}{F_c}$$

and Eq. (3) into Eq. (4) leads to:

$$F_s = m_1 \cdot F_c + Km_2 \cdot F_c + m_3 \cdot \frac{1+\sqrt{\gamma F_c^2+1}}{\lambda} \quad (5)$$

The fitting relationship between the displacement $\zeta$ of the characteristic point and the cohesion reduction factor $F_c$ is a hyperbolic equation as follows:

$$\zeta = \frac{\lambda b + c\left[\lambda(m_1+Km_2)\cdot F_c + m_3\left(1+\sqrt{1+\gamma F_c^2}\right)\right]}{\lambda + a\left[\lambda(m_1+Km_2)\cdot F_c + m_3\left(1+\sqrt{1+\gamma F_c^2}\right)\right]} \quad (6)$$

where, a, b, c, $m_1$, $m_2$, $m_3$ are undetermined coefficients, and $\zeta$ is the characteristic point displacement of the slope.

The method further includes: fitting the displacement curve of the characteristic point of the slope by using a Least Squares (LS) method yields a, b, c, $m_1$, $m_2$, $m_3$; substituting $m_1$, $m_2$, $m_3$ into Eq. (5) leads to the relational expression between the comprehensive safety factor $F_s$ and the cohesion reduction factor $F_c$, and substituting a, b, c, $m_1$, $m_2$, $m_3$ into Eq. (6) leads to the relational expression between the displacement $\zeta$ of the characteristic point and the cohesion reduction factor $F_c$.

The present disclosure has the following beneficial effects. Compared with the existing strength reduction method, the present disclosure considers the influence of the tensile strength on the slope stability, and reflects the difference in the attenuation and contribution of the cohesion, the internal friction angle and the tensile strength in the process of slope instability by different reduction factors.

Based on the sudden change of the characteristic point displacement of the slope as a criterion of slope instability, the present disclosure derives the fitting relationship between the characteristic point displacement and the cohesion reduction factor, which has sufficient theoretical basis and clear physical meaning. The present disclosure assumes that the comprehensive safety factor satisfies a linear relationship with the cohesion reduction factor, the internal friction angle reduction factor and the tensile strength reduction factor, and derives the relationship between the comprehensive safety factor and the cohesion reduction factor (simple and clear). Finally, the present disclosure summarizes and proposes an improved strength reduction method, that is, the three-parameter strength reduction method, and provides the steps for analyzing the slope stability through this method. The present disclosure provides a new reliable analysis method for slope stability evaluation.

DETAILED DESCRIPTION OF PREFERRED EMBODIMENTS

Embodiment 1

Figure 1:
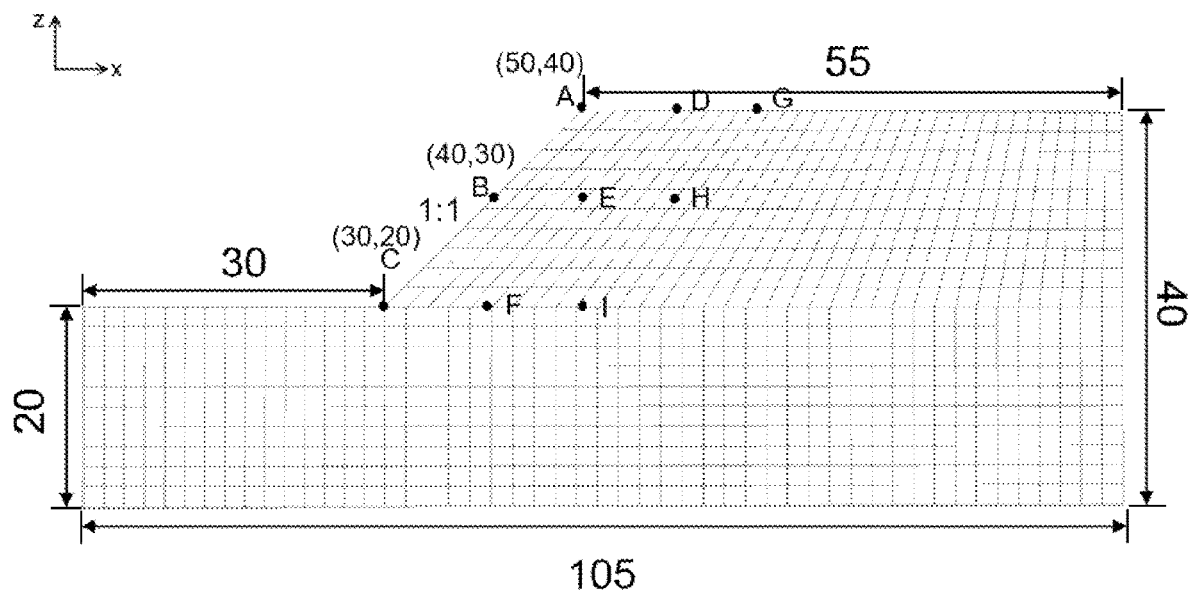
FIG. 1 is a slope calculation model (unit: m) provided by Embodiment 1 of the present disclosure.

This embodiment discloses a three-parameter strength reduction method for slope stability evaluation. First, a cohesion and an internal friction angle of a rock-soil mass of a slope are determined according to Eq. (7).

$$\begin{cases} c_i = \dfrac{c}{F_{ci}} \\ \varphi_i = \arctan\left(\dfrac{\tan\varphi}{F_{\varphi i}}\right) = \arctan\left(\dfrac{\tan\varphi}{F_{ci}\times K}\right) \end{cases} \quad (7)$$

In the Eq. (7), c, $\varphi$ represent an initial cohesion and internal friction angle of the rock-soil mass, respectively; $c_i$, $\varphi_i$ represent a corresponding cohesion and internal friction angle in an i-th reduction step, respectively; $F_{ci}$, $F_{\varphi i}$ represent a cohesion reduction factor and the internal friction angle in the i-th reduction step, respectively; K is a mechanism of matching reduction, which represents a difference in an attenuation between the cohesion and the internal friction angle; when K is greater than 1, the internal friction angle attenuates faster; when K is less than 1, the cohesion attenuates faster.

In calculation, step 1, the internal friction angle and the cohesion are reduced respectively to obtain the reduction factors $F_\varphi$ and $F_c$:

$$F_c = c/c' \quad (8)$$

$$F_\varphi = \tan\varphi/\tan\varphi' = K \times F_c$$

Then, $K = F_\varphi/F_c$ is calculated.

Step 2, the reduced shear strength parameters $c_i$ and $\varphi_i$ of the rock-soil mass are substituted into a uniaxial tensile strength expression (9) derived from a Mohr-Coulomb criterion:

$$\sigma_t = \sigma_3 = \frac{2c}{\sqrt{N_\varphi}} = \frac{2c\cos\varphi}{1+\sin\varphi} = \frac{2c}{\tan\varphi + \sqrt{1+\tan^2\varphi}} \quad (9)$$

The tensile strength obtained based on the reduced shear strength parameters is shown in Eq. (10):

$$\sigma_{ti} = \frac{2c_i}{\tan\varphi_i + \sqrt{1+\tan^2\varphi_i}} = \frac{\lambda\sigma_t}{1+\sqrt{\gamma F_{ci}^2 + 1}} \quad (10)$$

In the Eq., $\sigma_t$ is an initial tensile strength of the rock-soil mass; $\sigma_{ti}$ is a corresponding tensile strength in an i-th reduction step; $\lambda = K + K\sqrt{1+\cot^2\varphi}$, $\gamma = K^2 \cdot \cot^2\varphi$, which are respectively a constant greater than 0.

The tensile strength before reduction is divided by the tensile strength after reduction to obtain a reduction factor $F_t$ of the tensile strength:

$$F_t = \frac{1+\sqrt{\gamma \cdot F_c^2 + 1}}{\lambda} \quad (11)$$

It can be seen from the above Eq. that $F_t$ is a function of $F_c$, and $F_t$ is a monotonically increasing function when $F_c > 0$, which meets the requirements of the reduction factor.

It can be seen from Eqs. (8) and (11) that both the internal friction angle reduction factor and the tensile strength reduction factor change with the change of the cohesion reduction factor. Therefore, the determination of three reduction factors becomes the determination of a single reduction factor, which is convenient for the realization of the method.

Step 3, an expression of a comprehensive safety factor $F_s$ of the slope is derived based on the reduction factors of c, $\varphi$, $\sigma_t$, where $F_s$ is determined based on a sudden change of a displacement of a characteristic point of the slope as a criterion of slope instability.

It is assumed that the comprehensive safety factor $F_s$ satisfies a linear relationship, namely Eq. (12) with $F_c$, $F_\varphi$, and $F_t$.

$$F_s = m_1 \cdot F_c + m_2 \cdot F_\varphi + m_3 \cdot F_t \quad (12)$$

In the Eq., $m_1$, $m_2$, $m_3$ are undetermined coefficients, and $F_c$, $F_\varphi$, $F_t$ are the reduction factors of c, $\varphi$, $\sigma_t$ respectively.

A derivation demonstrates that $F_\varphi$, and $F_t$ both are functions of $F_c$, which satisfy Eq. (13).

$$F_\varphi = K \times F_c, \quad F_t = \frac{1+\sqrt{\gamma \cdot F_c^2 + 1}}{\lambda} \quad (13)$$

Substituting Eq. (13) into Eq. (12) leads to the expression of the comprehensive safety factor as follows:

$$F_s = m_1 \cdot F_c + Km_2 \cdot F_c + m_3 \cdot \frac{1+\sqrt{\gamma F_c^2 + 1}}{\lambda} \quad (14)$$

Step 4, the comprehensive safety factor $F_s$ of the slope is determined based on the reduction factors of c, $\varphi$, $\sigma_t$ and the criterion of slope instability, that is, the sudden change of the characteristic point.

The actual landslide observation data shows that when the characteristic point displacement of the slope changes suddenly, a corresponding slope failure occurs. That is, there is a certain functional relationship between the characteristic point displacement and the comprehensive safety factor, namely, $\zeta = h(F_s)$. For the convenience of calculation, a relationship between the displacement $\zeta$ of the characteristic point and the cohesion reduction factor $F_c$ is established according to Eq. (15), namely, $\zeta = f(F_s)$ The analysis of the change characteristics of an actual displacement curve indicates that as the reduction factor increases, the displacement gradually increases. When a certain threshold is reached, the displacement has a rapid increase process, which is a process in which damage occurs locally on the slope and the damaged area develops rapidly. At this time, the derivative function of the displacement curve also has a sudden increase process, which shows that the displacement curve is an unbounded function. Therefore, a hyperbolic equation is chosen to fit the relationship between the characteristic point displacement and the cohesion reduction factor, as shown in Eq. (15).

$$\xi = \frac{\lambda b + c\left[\lambda(m_1 + Km_2) \cdot F_c + m_3\left(1+\sqrt{1+\gamma F_c^2}\right)\right]}{\lambda + a\left[\lambda(m_1 + Km_2) \cdot F_c + m_3\left(1+\sqrt{1+\gamma F_c^2}\right)\right]} \quad (15)$$

In the Eq., a, b, c, $m_1$, $m_2$, $m_3$ are undetermined coefficients, and is the characteristic point displacement of the slope.

The method further includes: fitting the displacement curve of the characteristic point of the slope by using a Least Squares (LS) method yields the undetermined coefficients a, b, c, $m_1$, $m_2$, $m_3$; substituting them into Eq. (14) leads to the relational expression between the comprehensive safety factor $F_s$ and the cohesion reduction factor $F_c$, and substituting them into Eq. (15) leads to the relational expression between the displacement $\zeta$ of the characteristic point and the cohesion reduction factor $F_c$. The slope is considered unstable based on the slope instability criterion when the characteristic point displacement of the slope changes suddenly. Then substituting $F_c$ into Eq. (14) yields the comprehensive safety factor $F_s$.

A slope stability evaluation method using the three-parameter strength reduction method includes the following steps:

1) Generalize a geological model of a slope and establish a calculation model.

2) Separately reduce a cohesion and an internal friction angle to obtain a mechanism of matching reduction K.

3) Select an initial cohesion reduction factor $F_c$, determine a reduction factor of the internal friction angle and the tensile strength according to Eqs. (8) and (11), and reduce the strength parameters of all units according to their respective reduction factors and perform an elastic-plastic calculation.

4) Take a sudden change of a characteristic point displacement as a criterion of slope instability; if there is no sudden change in a displacement curve, gradually increase the reduction factor $F_c$ until a sudden change of the displacement curve appears.

5) Record the characteristic point displacement of the slope under different reduction factors, fit the displacement data according to Eq. (15), substitute the $m_1$, $m_2$, $m_3$ obtained by fitting into Eq. (14) to establish a relationship between a comprehensive safety factor and $F_c$, and take the corresponding $F_c$ in case of a sudden change in the displacement to calculate a critical comprehensive safety factor $F_s$.

The present disclosure is described in detail below with reference to the specific embodiment.

Embodiment: For a slope with a height of 40 m and an angle of 45°, a total of 9 characteristic points (A to I) are set. The specific size of the slope is shown in FIG. 1. In the embodiment of the present disclosure, the elastic-plastic calculation is performed by using the finite difference software Fast Lagrangian Analysis of Continua in 3 Dimensions (FLAC$^{3D}$). The calculation model has a total of 1,842 nodes and 850 units. The slope is only affected by gravity. The boundary conditions include normal constraints on both left and right sides of the slope and an integrity constraint on the bottom of the slope. The specific physical and mechanical parameters of the rock-soil mass are shown in Table 1 below.

TABLE 1

Physical and mechanical parameters of rock-soil mass in the embodiment

| Unit weight/ (kN/m$^3$) | Elastic modulus/ MPa | Poisson's ratio ν | Cohesion/ kPa | Internal friction angle/(°) | Tensile strength/ kPa |
|---|---|---|---|---|---|
| 25 | 100 | 0.3 | 42 | 17 | 10 |

Through the FLAC$^{3D}$ software, the safety factor is calculated by separately reducing the cohesion and internal friction angle. The matching reduction factor is K=1.04. According to Eqs. (8) and (11), the reduction factors of the internal friction angle and the tensile strength in each calculation step are determined:

$$F_{\varphi i} = 1.04 F_{ci} \tag{16}$$

$$F_{ti} = \frac{1 + \sqrt{3.402 F_{ci}^2 + 1}}{4.597}$$

$F_c$ is continuously adjusted. The total displacement of point A on the top of the slope is recorded, and a curve of the total displacement of the characteristic point and $F_c$ is established. LS fitting of the curve is performed by using MATLAB, with a correlation coefficient as follows:

$$R = \left| \frac{\sum_{i=1}^{n}(F_{ci} - \overline{F}_c)(\xi_i - \overline{\xi})}{\sqrt{\sum_{i=1}^{n}(F_{ci}^2 - n\overline{F}_c^2)} \cdot \sqrt{\sum_{i=1}^{n}(\xi_i^2 - n\overline{\xi}^2)}} \right| \tag{17}$$

In the Eq., n represents reduction time steps; $F_{ci}$, $\zeta_i$ represent the cohesion reduction factor and the characteristic point displacement at the i-th step respectively; $\overline{F}_c$, $\overline{\zeta}$ represent a mean of $F_{ci}$, $\zeta_i$, respectively.

Figure 2:
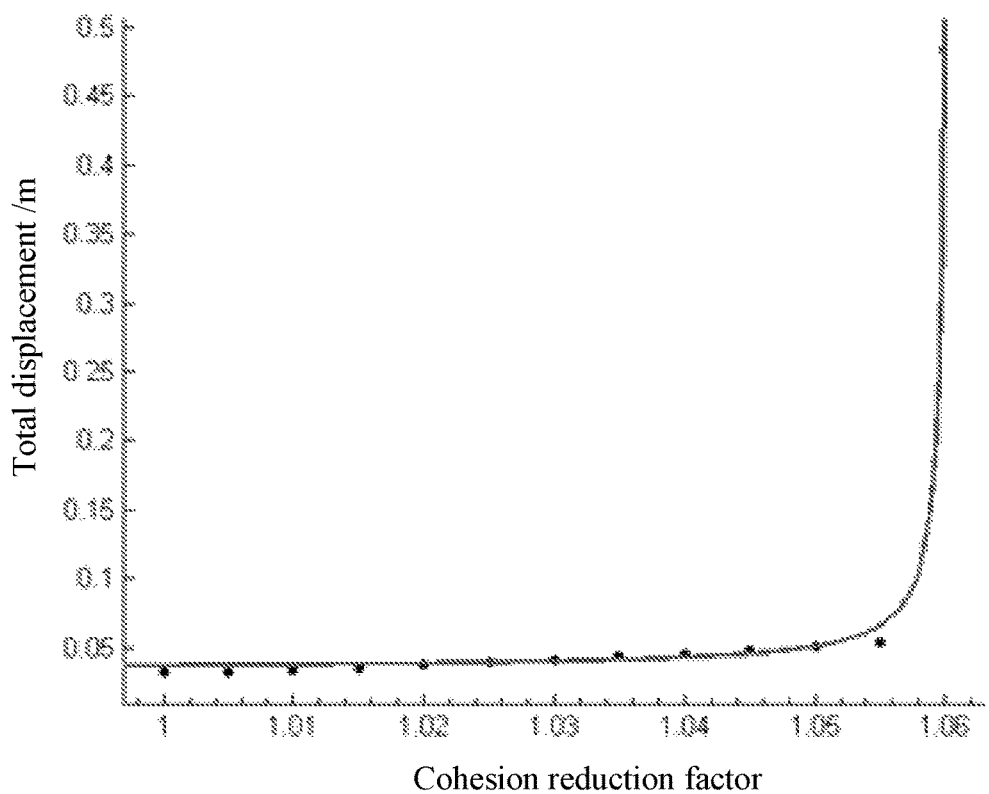
FIG. 2 is a displacement fitting curve of a characteristic point A of a slope according to Embodiment 1 of the present disclosure.

The calculation results are shown in Table 2, and the fitted curve is shown in FIG. 2. $R^2$ is close to 1, which shows that Eq. (15) fits the data well. The shape of the fitted curve also conforms to the displacement rule, which proves that the fitting equation can be used to characterize the functional relationship between the total displacement and the cohesion reduction factor $F_c$. According to the fitted curve, it can be roughly determined that the displacement starts to change suddenly when $F_c$=1.056. By substituting the fitting parameters $m_1$, $m_2$, $m_3$ and $F_c$ into Eq. (14), the comprehensive safety factor corresponding to curve A is 1.089.

TABLE 2

Fitted data of displacement curve

| Point No. | a | b | c | $m_1$ | $m_2$ | $m_3$ | $R^2$ |
|---|---|---|---|---|---|---|---|
| A | −0.914 | 0.0347 | −0.03161 | 0.4073 | 0.4378 | 0.1739 | 0.9986 |

The comprehensive safety factors determined by different strength reduction methods are shown in Table 3.

TABLE 3

Comparison of comprehensive safety factors determined by different strength reduction

| Method | Traditional strength reduction method | Traditional strength reduction method considering tensile failure | Simplified Bishop Method | Method of the present disclosure |
|---|---|---|---|---|
| Comprehensive safety factor | 1.128 | 1.098 | 1.064 | 1.089 |

It can be seen from the table that the comprehensive safety factor obtained by the method of the present disclosure is 1.089, which is close to the calculation result obtained by the simplified Bishop method, and is smaller than those of the traditional strength reduction method and the traditional strength reduction method considering tensile failure. The traditional strength reduction method does not consider the different attenuation of cohesion and internal friction angle, and the traditional strength reduction method considering tensile failure does not consider the influence of the tensile strength reduction factor on the comprehensive safety factor, so the calculation results are all too large. This also shows that the comprehensive safety factor calculated by the method of the present disclosure is more accurate and reliable.

Embodiment 2

This embodiment is a specific implementation of Embodiment 1.

Figure 3:
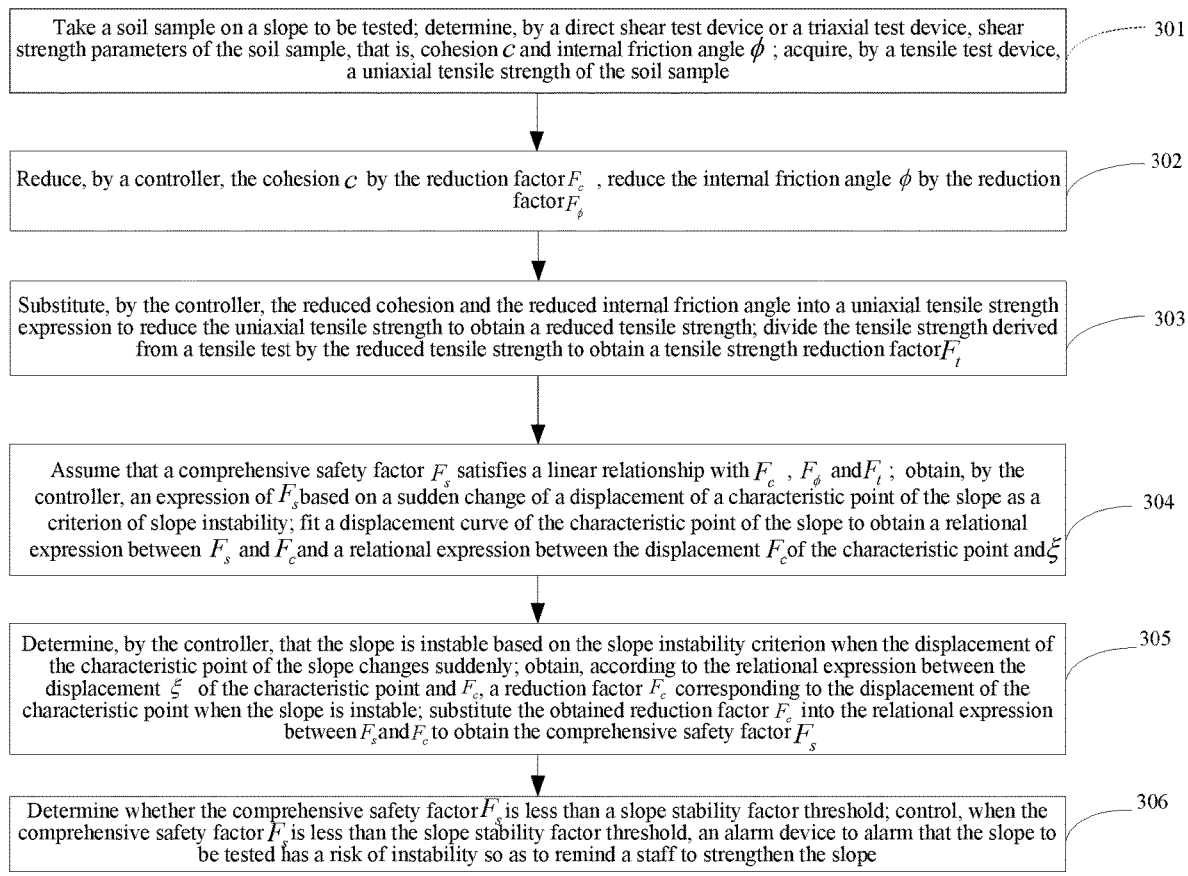
FIG. 3 is a flowchart of a three-parameter strength reduction method for slope stability evaluation of Embodiment 2 of the present disclosure.

Specifically, as shown in FIG. 3, a three-parameter strength reduction method for slope stability evaluation is provided, including:

step 301, take a soil sample on a slope to be tested; determine, by a direct shear test device or a triaxial test device, shear strength parameters of the soil sample, that is, cohesion c and internal friction angle φ; acquire, by a tensile test device, a uniaxial tensile strength of the soil sample;

step 302, read, by a controller, a reduction factor $F_c$ and a reduction factor $F_\varphi$ from a first memory; reduce the cohesion c by the reduction factor $F_c$, reduce the internal friction angle φ by the reduction factor $F_\varphi$; give a mechanism of matching reduction $$K = \frac{F_\varphi}{F_c}$$

to obtain a relational expression of $F_\varphi$ and $F_c$; store a reduced cohesion and a reduced internal friction angle in a register;

step 303, read, by the controller, the reduced cohesion and the reduced internal friction angle from the register; substitute the reduced cohesion and the reduced internal friction angle into a uniaxial tensile strength expression to reduce the uniaxial tensile strength to obtain a reduced tensile strength; divide the tensile strength derived from a tensile test by the reduced tensile strength to obtain a tensile strength reduction factor $F_t$; store the tensile strength reduction factor $F_t$ in the register;

step 304, assume that a comprehensive safety factor $F_s$ satisfies a linear relationship with $F_c$, $F_\varphi$, $F_t$, read, by the controller, the reduction factor $F_c$ and the reduction factor $F_\varphi$ from the first memory; read the tensile strength reduction factor $F_t$ from the register; then obtain an expression of $F_s$ based on a sudden change of a displacement of a characteristic point of the slope as a criterion of slope instability; fit a displacement curve of the characteristic point of the slope to obtain a relational expression between $F_s$ and $F_c$ and a relational expression between the displacement ζ of the characteristic point and $F_c$; save the relational expression between $F_s$ and $F_c$ and the relational expression between the displacement ζ of the characteristic point and $F_c$ in a second memory;

step 305, determine, by the controller, that the slope is instable based on the slope instability criterion when the displacement of the characteristic point of the slope changes suddenly; read the relational expression between $F_s$ and $F_c$ and the relational expression between the displacement ζ of the characteristic point and $F_c$ from the second memory; obtain, according to the relational expression between the displacement ζ of the characteristic point and $F_c$, a reduction factor $F_c$ corresponding to the displacement of the characteristic point when the slope is instable; substitute the obtained reduction factor $F_c$ into the relational expression between $F_s$ and $F_c$ to obtain the comprehensive safety factor $F_s$; save the comprehensive safety factor $F_s$ in the register; and step 306, read, by the controller, the comprehensive safety factor $F_s$ from the register; determine whether the comprehensive safety factor $F_s$ is less than a slope stability factor threshold; control, when the comprehensive safety factor $F_s$ is less than the slope stability factor threshold, an alarm device to alarm that the slope to be tested has a risk of instability so as to remind a staff to strengthen the slope.

In this embodiment, the uniaxial tensile strength expression is:

$$\sigma_t = \frac{2c}{\tan\varphi + \sqrt{1 + \tan^2\varphi}} \quad (1)$$

where, $\sigma_t$ is an initial tensile strength of a rock-soil mass, and the reduced tensile strength is shown in Eq. (2):

$$\sigma_{ti} = \frac{2c}{\tan\varphi_i + \sqrt{1 + \tan^2\varphi_i}} = \frac{\lambda \sigma_t}{1 + \sqrt{\gamma F_{ci}^2 + 1}} \quad (2)$$

where, $\sigma_{ti}$ is a corresponding tensile strength in an i-th reduction step; $c_i$, $\varphi_i$ are corresponding cohesion and internal friction angle in the i-th reduction step, respectively; $F_{ci}$ is a cohesion reduction factor in the i-th reduction step; $\lambda = K + K\sqrt{1 + \cot^2\varphi}$, $\gamma = K^2 \cdot \cot^2\varphi$, which are respectively a constant greater than 0;

the tensile strength reduction factor $F_t$ is:

$$F_t = \frac{1 + \sqrt{\gamma \cdot F_c^2 + 1}}{\lambda} \quad (3)$$

In this embodiment, the linear relationship between the comprehensive safety factor $F_s$ and $F_c$, $F_\varphi$ and $F_t$ is:

$$F_s = m_1 \cdot F_c + m_2 \cdot F_\varphi + m_3 \cdot F_t \quad (4)$$

where, $m_1$, $m_2$, $m_3$ are undetermined coefficients, and substituting $$K = \frac{F_\varphi}{F_c}$$

and Eq. (3) into Eq. (4) leads to:

$$F_s = m_1 \cdot F_c + Km_2 \cdot F_c + m_3 \cdot \frac{1 + \sqrt{\gamma F_c^2 + 1}}{\lambda} \quad (5)$$

the fitting relationship between the displacement ζ of the characteristic point of the slope and the cohesion reduction factor $F_c$ adopts a hyperbolic equation as follows:

$$\xi = \frac{\lambda b + c\left[\lambda(m_1 + Km_2) \cdot F_c + m_3\left(1 + \sqrt{1 + \gamma F_c^2}\right)\right]}{\lambda + a\left[\lambda(m_1 + Km_2) \cdot F_c + m_3\left(1 + \sqrt{1 + \gamma F_c^2}\right)\right]} \quad (6)$$

where, a, b, c, $m_2$, $m_3$ are undetermined coefficients, and is the displacement of the characteristic point of the slope;

fit the displacement curve of the characteristic point of the slope by using a LS method yields a, b, c, $m_1$, $m_2$, $m_3$; substitute $m_1$, $m_2$, $m_3$ into Eq. (5) leads to the relational expression between the comprehensive safety factor $F_s$ and the cohesion reduction factor $F_c$, and substitute a, b, c, $m_2$, $m_3$ into Eq. (6) leads to the relational expression between the displacement of the characteristic point and the cohesion reduction factor $F_c$.

Embodiment 3

This embodiment describes the system used to implement the method in Embodiment 2.

Figure 4:
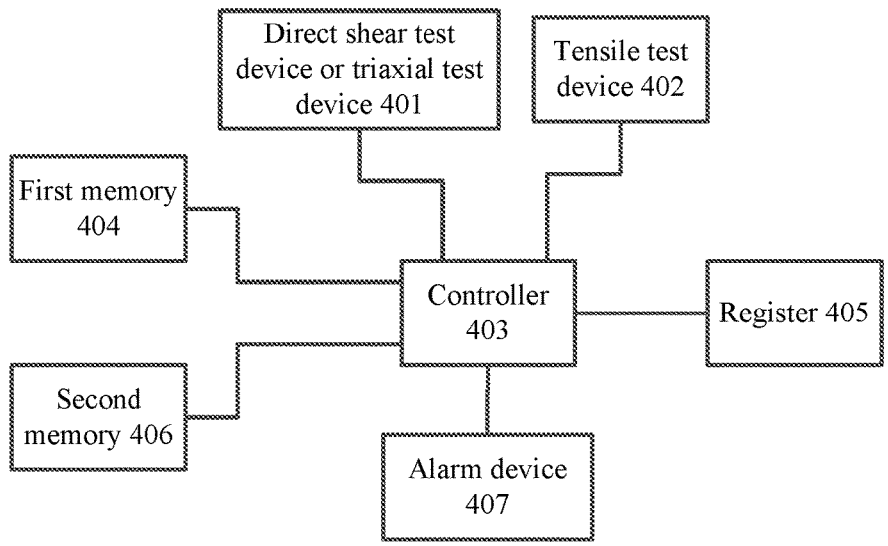
FIG. 4 is a schematic diagram of a three-parameter strength reduction system for slope stability evaluation of Embodiment 3 of the present disclosure.

Specifically, as shown in FIG. 4, a three-parameter strength reduction system for slope stability evaluation is provided. The system includes a direct shear test device or a triaxial test device 401, a tensile test device 402, a controller 403, a first memory 404, a register 405, a second memory 406 and an alarm device 407.

The direct shear test device or the triaxial test device is connected to the controller; the direct shear test device or the triaxial test device is used to perform a shear test or a triaxial test on a soil sample taken from a slope to be tested to obtain shear strength parameters of the soil sample, that is, cohesion c and internal friction angle φ, and send the cohesion c and the internal friction angle φ to the controller.

The tensile test device is connected to the controller; the tensile test device is used to perform a tensile test on the soil sample of the slope to be tested to obtain a uniaxial tensile strength of the soil sample, and send the uniaxial tensile strength to the controller;

The first memory is connected to the controller, and the first memory is used to store a reduction factor $F_c$ and a reduction factor $F_\varphi$.

The second memory is connected to the controller, and the second memory is used to store a relational expression between $F_s$ and $F_c$ and a relational expression between a displacement ζ of a characteristic point and $F_c$ calculated by the controller.

The register is connected to the controller, and the register is used to store a reduced cohesion, a reduced internal friction angle, a tensile strength reduction factor $F_t$ and a comprehensive safety factor $F_s$ calculated by the controller.

The controller is used to read the reduction factor $F_c$ and the reduction factor $F_\varphi$ from the first memory, reduce the cohesion c by the reduction factor $F_c$, reduce the internal friction angle φ by the reduction factor $F_\varphi$, give a mechanism of matching reduction $$K = \frac{F_\varphi}{F_c}$$

to obtain a relational expression of $F_\varphi$ and $F_c$, and store the reduced cohesion and the reduced internal friction angle in the register.

The controller is further used to read the reduced cohesion and the reduced internal friction angle from the register, substitute the reduced cohesion and the reduced internal friction angle into a uniaxial tensile strength expression to reduce the uniaxial tensile strength to obtain a reduced tensile strength, divide a tensile strength derived from a tensile test by the reduced tensile strength to obtain a tensile strength reduction factor $F_t$, and store the tensile strength reduction factor $F_t$ in the register.

The controller is further used to assume that the comprehensive safety factor $F_s$ satisfies a linear relationship with $F_c$, $F_\varphi$ and $F_t$, read the reduction factor $F_c$ and the reduction factor $F_\varphi$ from the first memory, read the tensile strength reduction factor $F_t$ from the register, then obtain an expression of $F_s$ based on a sudden change of the displacement of the characteristic point of the slope as a criterion of slope instability, fit a displacement curve of the characteristic point of the slope to obtain a relational expression between $F_s$ and $F_c$ and a relational expression between the displacement ζ of the characteristic point and $F_c$, save the relational expression between $F_s$ and $F_c$ and the relational expression between the displacement ζ of the characteristic point and $F_c$ in the second memory.

The controller is further connected to the alarm device, and the controller is further used to read the comprehensive safety factor $F_s$ from the register, determine whether the comprehensive safety factor $F_s$ is less than a slope stability factor threshold, and control, when the comprehensive safety factor $F_s$ is less than the slope stability factor threshold, the alarm device to alarm that the slope to be tested has a risk of instability so as to remind a staff to strengthen the slope.

Each embodiment in the specification of the present disclosure is described in a progressive manner. Each embodiment focuses on the difference from other embodiments, and the same and similar parts between the embodiments may refer to each other.

In this specification, several specific embodiments are used for illustration of the principles and implementations of the present disclosure. The description of the foregoing embodiments is used to help illustrate the method of the present disclosure and the core ideas thereof. In addition, those of ordinary skill in the art can make various modifications in terms of specific implementations and the scope of application in accordance with the ideas of the present disclosure. Therefore, the content of this specification shall not be construed as a limitation to the present disclosure.

What is claimed is:

1. A three-parameter strength reduction method for slope stability evaluation, comprising:

step 1, taking a soil sample on a slope to be tested; determining, by a direct shear test device or a triaxial test device, shear strength parameters of the soil sample, that is, cohesion c and internal friction angle φ; acquiring, by a tensile test device, a uniaxial tensile strength of the soil sample;

step 2, reading, by a controller, a reduction factor $F_c$ and a reduction factor $F_\varphi$ from a first memory; reducing the cohesion c by the reduction factor $F_c$, reducing the internal friction angle φ by the reduction factor $F_\varphi$; giving a mechanism of matching reduction $$K = \frac{F_\varphi}{F_c}$$

to obtain a relational expression of $F_\varphi$ and $F_c$; storing a reduced cohesion and a reduced internal friction angle in a register;

step 3, reading, by the controller, the reduced cohesion and the reduced internal friction angle from the register; substituting the reduced cohesion and the reduced internal friction angle into a uniaxial tensile strength expression to reduce the uniaxial tensile strength to obtain a reduced tensile strength; dividing the tensile strength derived from a tensile test by the reduced tensile strength to obtain a tensile strength reduction factor $F_t$; storing the tensile strength reduction factor $F_t$ in the register;

step 4, assuming that a comprehensive safety factor $F_s$ satisfies a linear relationship with $F_c$, $F_\varphi$ and $F_t$; reading, by the controller, the reduction factor $F_c$ and the reduction factor $F_\varphi$ from the first memory; reading the tensile strength reduction factor $F_t$ from the register; then obtaining an expression of $F_s$, based on a sudden change of a displacement of a characteristic point of the slope as a criterion of slope instability; fitting a displacement curve of the characteristic point of the slope to obtain a relational expression between $F_s$ and $F_c$ and a relational expression between the displacement ζ of the characteristic point and $F_c$; saving the relational expression between $F_s$ and $F_c$ and the relational expression between the displacement $\zeta$ of the characteristic point and $F_c$ in a second memory;

step 5, determining, by the controller, that the slope is instable based on the slope instability criterion when the displacement of the characteristic point of the slope changes suddenly; reading the relational expression between $F_s$ and $F_c$ and the relational expression between the displacement $\zeta$ of the characteristic point and $F_c$ from the second memory; obtaining, according to the relational expression between the displacement $\zeta$ of the characteristic point and $F_c$, a reduction factor $F_c$ corresponding to the displacement of the characteristic point when the slope is instable; substituting the obtained reduction factor $F_c$ into the relational expression between $F_s$ and $F_c$ to obtain the comprehensive safety factor $F_s$; saving the comprehensive safety factor $F_s$, in the register; and step 6, reading, by the controller, the comprehensive safety factor $F_s$ from the register; determining whether the comprehensive safety factor $F_s$ is less than a slope stability factor threshold; controlling, when the comprehensive safety factor $F_s$, is less than the slope stability factor threshold, an alarm device to alarm that the slope to be tested has a risk of instability so as to remind a staff to strengthen the slope.

2. The three-parameter strength reduction method for slope stability evaluation according to claim 1, wherein the uniaxial tensile strength expression is:

$$\sigma_t = \frac{2c}{\tan\varphi + \sqrt{1+\tan^2\varphi}} \tag{1}$$

wherein, $\sigma_t$ is an initial tensile strength of a rock-soil mass, and the reduced tensile strength is shown in Eq. (2):

$$\sigma_{ti} = \frac{2c_i}{\tan\varphi_i + \sqrt{1+\tan^2\varphi_i}} = \frac{\lambda\sigma_t}{1+\sqrt{\gamma F_{ci}^2+1}} \tag{2}$$

wherein, $\sigma_{ti}$ is a corresponding tensile strength in an i-th reduction step; $c_i$, $\varphi_i$, are corresponding cohesion and internal friction angle in the i-th reduction step, respectively; $F_{ci}$ is a cohesion reduction factor in the i-th reduction step; $\lambda = K+K\sqrt{1+\cot^2\varphi}$, $\gamma=K^2\cdot\cot^2\varphi$, which are respectively a constant greater than 0;

the tensile strength reduction factor $F_t$ is:

$$F_t = \frac{1+\sqrt{\gamma\cdot F_c^2+1}}{\lambda}. \tag{3}$$

3. The three-parameter strength reduction method for slope stability evaluation according to claim 2, wherein the linear relationship between the comprehensive safety factor $F_s$ and $F_c$, $F_\varphi$ and $F_t$ is:

$$F_s = m_1\cdot F_c + m_2\cdot F_\varphi + m_3\cdot F_t \tag{4}$$

wherein, $m_1$, $m_2$, $m_3$ are undetermined coefficients, and substituting $$K = \frac{F_\varphi}{F_c}$$

and Eq. (3) into Eq. (4) leads to:

$$F_s = m_1\cdot F_c + Km_2\cdot F_c + m_3\cdot \frac{1+\sqrt{\gamma F_c^2+1}}{\lambda} \tag{5}$$

the fitting relationship between the displacement $\zeta$ of the characteristic point of the slope and the cohesion reduction factor $F_c$ adopts a hyperbolic equation as follows:

$$\xi = \frac{\lambda b + c\left[\lambda(m_1+Km_2)\cdot F_c + m_3\left(1+\sqrt{1+\gamma F_c^2}\right)\right]}{\lambda + a\left[\lambda(m_1+Km_2)\cdot F_c + m_3\left(1+\sqrt{1+\gamma F_c^2}\right)\right]} \tag{6}$$

wherein, a, b, c, $m_1$, $m_2$, $m_3$ are undetermined coefficients, and $\zeta$ is the displacement of the characteristic point of the slope;

fitting the displacement curve of the characteristic point of the slope by using a LS method yields a, b, c, $m_1$, $m_2$, $m_3$; substituting $m_1$, $m_2$, $m_3$ into Eq. (5) leads to the relational expression between the comprehensive safety factor $F_s$ and the cohesion reduction factor $F_c$, and substituting a, b, c, $m_1$, $m_2$, $m_3$ into Eq. (6) leads to the relational expression between the displacement $\zeta$ of the characteristic point and the cohesion reduction factor $F_c$.

4. A three-parameter strength reduction system for slope stability evaluation, wherein the system comprises a direct shear test device or a triaxial test device, a tensile test device, a controller, a first memory, a register, a second memory and an alarm device;

the direct shear test device or the triaxial test device is connected to the controller; the direct shear test device or the triaxial test device is used to perform a shear test or a triaxial test on a soil sample taken from a slope to be tested to obtain shear strength parameters of the soil sample, that is, cohesion c and internal friction angle $\varphi$, and send the cohesion c and the internal friction angle $\varphi$ to the controller;

the tensile test device is connected to the controller; the tensile test device is used to perform a tensile test on the soil sample of the slope to be tested to obtain a uniaxial tensile strength of the soil sample, and send the uniaxial tensile strength to the controller;

the first memory is connected to the controller, and the first memory is used to store a reduction factor $F_c$ and a reduction factor $F_\varphi$;

the second memory is connected to the controller, and the second memory is used to store a relational expression between $F_s$ and $F_c$ and a relational expression between a displacement $\zeta$ of a characteristic point and $F_c$ calculated by the controller;

the register is connected to the controller, and the register is used to store a reduced cohesion, a reduced internal friction angle, a tensile strength reduction factor $F_t$ and a comprehensive safety factor $F_s$ calculated by the controller;

the controller is used to read the reduction factor $F_c$ and the reduction factor $F_\varphi$ from the first memory, reduce the cohesion c by the reduction factor $F_c$, reduce the internal friction angle $\varphi$ by the reduction factor $F_\varphi$, give a mechanism of matching reduction $$K = \frac{F_\varphi}{F_c}$$

to obtain a relational expression of $F_\varphi$ and $F_c$, and store the reduced cohesion and the reduced internal friction angle in the register;

the controller is further used to read the reduced cohesion and the reduced internal friction angle from the register, substitute the reduced cohesion and the reduced internal friction angle into a uniaxial tensile strength expression to reduce the uniaxial tensile strength to obtain a reduced tensile strength, divide a tensile strength derived from a tensile test by the reduced tensile strength to obtain a tensile strength reduction factor $F_t$, and store the tensile strength reduction factor $F_t$ in the register;

the controller is further used to assume that the comprehensive safety factor $F_s$ satisfies a linear relationship with $F_c$, $F_\varphi$ and $F_t$, read the reduction factor $F_c$ and the reduction factor $F_\varphi$ from the first memory, read the tensile strength reduction factor $F_t$ from the register, then obtain an expression of $F_s$ based on a sudden change of the displacement of the characteristic point of the slope as a criterion of slope instability, fit a displacement curve of the characteristic point of the slope to obtain a relational expression between $F_s$ and $F_c$ and a relational expression between the displacement $\zeta$ of the characteristic point and $F_c$, save the relational expression between $F_s$ and $F_c$ and the relational expression between the displacement $\varphi$ of the characteristic point and $F_c$ in the second memory;

the controller is further connected to the alarm device, and the controller is further used to read the comprehensive safety factor $F_s$ from the register, determine whether the comprehensive safety factor $F_s$ is less than a slope stability factor threshold, and control, when the comprehensive safety factor $F_s$ is less than the slope stability factor threshold, the alarm device to alarm that the slope to be tested has a risk of instability so as to remind a staff to strengthen the slope.

* * * * *